United States Patent [19]

Chandra et al.

[11] Patent Number: 4,559,227
[45] Date of Patent: Dec. 17, 1985

[54] CONDITIONING SHAMPOO CONTAINING AMINE FUNCTIONAL POLYDIORGANOSILOXANE

[75] Inventors: Grish Chandra; Gretchen S. Kohl, both of Midland, Mich.; James A. Tassoff, West Caldwell, N.J.

[73] Assignee: Dow Corning Corporation, Midland, Mich.

[21] Appl. No.: 666,849

[22] Filed: Oct. 31, 1984

[51] Int. Cl.$^4$ ............................................. A61K 7/06
[52] U.S. Cl. ........................... 424/70; 424/DIG. 4; 424/59; 424/60; 424/78; 424/81
[58] Field of Search ........................................ 424/70

[56] References Cited

U.S. PATENT DOCUMENTS

| | | | |
|---|---|---|---|
| 4,185,087 | 1/1980 | Morlino | 424/70 |
| 4,342,742 | 8/1982 | Sebag et al. | 424/59 |
| 4,426,310 | 1/1984 | Verunica | 424/70 |
| 4,450,152 | 5/1984 | Ona et al. | 424/DIG. 5 |
| 4,452,732 | 6/1984 | Bolich, Jr. | 424/70 |

FOREIGN PATENT DOCUMENTS

| | | | |
|---|---|---|---|
| 2912485 | 10/1980 | Fed. Rep. of Germany | 424/70 |
| 2912484 | 10/1980 | Fed. Rep. of Germany | 424/70 |
| 66506 | 5/1980 | Japan | 424/70 |
| 0022717 | 3/1981 | Japan | 424/70 |
| 0119998 | 7/1982 | Japan | 424/70 |
| 1598567 | 9/1981 | United Kingdom | 424/70 |

OTHER PUBLICATIONS

A. Hunting, Encyclopedia of Shampoo Ingredients, pp. 40 and 143, (1983), Micelle Press Inc., Cranford, NH 07016.

Primary Examiner—Dale R. Ore
Attorney, Agent, or Firm—James E. Bittell

[57] ABSTRACT

A conditioning shampoo composition is disclosed containing a nonionic surfactant of the alkanolamide or amine oxide type, an amine functional methylsiloxane polymer, a detersive surfactant of the anionic or amphoteric type, and water. A method of preparing the shampoo composition as a stable solution is also disclosed. During use, the shampoo composition simultaneously cleanses the hair and deposits the siloxane polymer conditioning component on the hair.

30 Claims, No Drawings

CONDITIONING SHAMPOO CONTAINING AMINE FUNCTIONAL POLYDIORGANOSILOXANE

BACKGROUND OF THE INVENTION

This invention relates to a hair shampoo composition which deposits a hair conditioning ingredient on the hair at the same time that oil and dirt are washed from the hair. In particular, it relates to a shampoo composition containing amine functional polydiorganosiloxane as a hair conditioning component.

Detersive surfactants used for washing hair do not distinguish between oil which is dirt or which exceeds requirements and oil which is essential for the proper care and appearance of hair. Unless the hair is washed with an extremely weak shampoo or very infrequently, it is desirable to return some oil or other material to the hair to "condition" it. For example, the use of after-shampoo conditioning products in order to return materials to hair which improve its characteristics and appearance is well known. However, it has been recognized for a long time that a shampoo that could simultaneously clean and deposit a conditioning substance on hair would be more efficient and convenient.

Unfortunately, conditioning substances which may be beneficially applied to hair in after-shampoo products are often ineffective or only marginally effective when used in shampoo compositions. The nature of the conditioning substance and the composition of the shampoo from which it is intended to be deposited are factors which affect the extent of conditioning benefits actually realized. Moreover, a conditioning substance when added to a shampoo formulation can cause problems such as reduced foaming, cloudiness, and instability which results in precipitation or separation of components.

Accordingly, it is a purpose of the present invention to provide improved conditioning shampoo compositions that simultaneously cleanse the hair and deposit a conditioning substance on the hair. Further it is a purpose of the present invention to provide conditioning shampoo compositions that effectively condition hair and at the same time provide the hair with a clean, non-greasy feeling. In addition, it is a purpose of the present invention to provide shampoo compositions in which the components form a stable, non-separating mixture.

It is taught in U.S. Pat. No. 4,342,742 to Sebag et al. that surface active polysiloxanes, represented by the formula

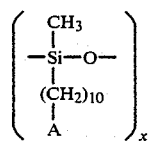

where x denotes an integer from 3 to 10 and A denotes a hydrophilic unit, are useful in cosmetic and pharmaceutical compositions, especially compositions for hair. Sebag et al. teach that the hydrophilic unit A can be cationic, zwitterionic, anionic or nonionic and may comprise amine, amine oxide, ammonium, ammonioalkylcarboxylate, ammonioalkylsulphate, amide, sulphonamide, ether, thioether, sulphoxide, hydroxyl, ester or acid groups. More specifically Sebag et al. teach a shampoo composition containing triethanolamine lauryl sulphate, lauryl diethanolamide, sufficient HCl to adjust the pH to 7.5, water, and a polysiloxane of the above formula where A denotes the —COOH group.

It is known from German Patent Application No. 2,912,485 to use certain quaternary nitrogen derivatives of polysiloxanes in hair shampoos to improve the wet combing, softness and body of the washed air. A shampoo composition is described containing 30% sodium lauryl ether sulfate (27/28% active), 2% NaCl, 2% coconut fatty acid diethanolamide, 5% of a 50% aqueous solution of silicone of the formula

where R is —(CH$_2$)$_{10}$OCONH(CH$_2$)$_3$N$^+$(CH$_3$)$_2$CH$_2$C$_6$H$_5$.Cl$^-$, 1% Zn pyridine-thione, 1% protein hydrolyzate, 1% perfume and 58% water. In addition, German Patent Application 2,912,484 teaches that certain polysiloxane polymers with side chains containing quaternary nitrogen groups are useful as components of hair washing or treating compositions. The quaternary nitrogen groups described as useful on the siloxane are the same as described in German Patent Application 2,912,485, but the groups are attached along the siloxane polymer chain instead of only at the ends of the siloxane chain. Useful siloxanes are reported to contain from 0-300 nonfunctional siloxane units and 1-75 quaternary nitrogen functional siloxane units.

Similarly, it is taught in Japanese Kokai Patent No. Sho 55[1980]-66506 that certain siloxane polymers with quaternary nitrogen contents of 0.7 to 5.5 weight percent can be employed as conditioning components in shampoo compositions. The quaternary nitrogen containing siloxanes are reported to form complex salts with anionic surfactants. These complex salts, however, are said to be soluble in a transparent state in aqueous solutions in the presence of the anionic surfactants.

In U.S. Pat. No. 4,185,087, Morlino teaches that certain quaternary nitrogen derivatives of trialkylamino hydroxy organosilicon polymers are useful in hair conditioning compositions and shampoos. The preferred siloxane polymers described by Morlino have the formula

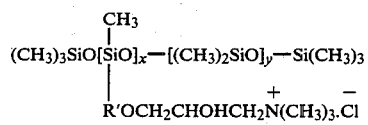

wherein x is 2 to 8, y is 20 to 50, and R' is a divalent alkylene having from 1 to 8 carbon atoms.

The quaternary nitrogen containing siloxanes described in the above references are generally water soluble or compatible and are reported to be easily formulated into clear shampoo compositions. While such shampoo compositions may provide some conditioning of hair as it is cleaned, there is still a need for further improvement. Moreover, the quaternary nitrogen containing siloxanes are difficult and complicated materials to prepare so that it would be advantageous if simpler, less costly siloxane polymers could be used in hair shampoo compositions.

Certain amine functional siloxanes such as amodimethicone are known to provide excellent hair conditioning when applied to hair from an aqueous emulsion after the hair has been shampooed. However, formulation difficulties are encountered when emulsions of amine functional siloxanes are added to shampoo compositions. The siloxane emulsion causes cloudiness and may be so unstable in the shampoo composition that phase separation occurs. Although the cloudiness may be disguised by using a pearling agent such as glycol stearate, shampoo compositions containing emulsions of amine functional siloxanes have not been completely satisfactory. However, the *Encyclopedia of Shampoo Ingredients* by Anthony L. L. Hunting, 1983, teaches that amodimethicone has been used as a component of a peallized (i.e., nonclear) shampoo composition. Amodimethicone is an amine substituted siloxane polymer containing reactive silanol (SiOH) functionality that is stabilized in an aqueous emulsion by a cationic and a nonionic surfactant. The siloxane polymer is represented by the formula

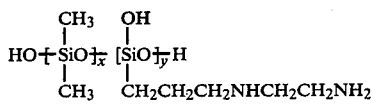

where x and y are numbers depending on the molecular weight of the polymer. When the emulsion is broken, the siloxane polymer is no longer stabilized and may crosslink and cure by condensation of the silanol groups.

United States application for patent, Ser. No. 595,224, filing date Mar. 30, 1984, and assigned to the same assignee as this present application, teaches that an aqueous emulsion containing an aminoalkyl substituted polydimethylsiloxane is useful as an after-shampoo hair conditioner because it facilitates combing and imparts a smooth feel to hair.

United States application for patent, Ser. No. 632,357, filing date July 19, 1984, and assigned to a subsidiary of the assignee of this present application, teaches a shampoo composition containing as essential components (1) a silane or a polydiorganosiloxane having a quaternary ammonium substituted group attached to silicon, (2) a polydiorganosiloxane having silicon-bonded substituents which are amine-substituted hydrocarbon groups, (3) one or more surfactants, and (4) water. An exemplary shampoo composition is shown containing linoleic diethanolamide and pearling agent as additional nonessential components. The amine functional siloxane (component 2) is added to the shampoo in the form of an aqueous emulsion. These shampoo compositions are reported to provide improved fullness and body to hair.

United States application for patent, Ser. No. 542,639, filing date Oct. 17, 1983, and assigned to the same assignee as this present application, teaches a method of preparing clear microemulsions of amine functional polyorganosiloxanes. It is further taught that transparent microemulsions of amine functional siloxanes can be mixed with a shampoo base of sodium lauryl ether sulfate and water to produce a stable, transparent composition.

SUMMARY OF THE INVENTION

The present invention relates to a shampoo composition for cleansing and conditioning hair. The shampoo composition comprises in the form of a solution, (A) 0.1 to 10 percent by weight of a nonionic surfactant selected from the group consisting of fatty acid alkanolamide surfactants and amine oxide surfactants, (B) 0.1 to 10 percent by weight of an amine functional siloxane polymer represented by the general formula

wherein R′ denotes an alkyl group of 1 to 4 carbons or a phenyl group, with the proviso that at least 50 percent of the total R′ groups are methyl; Q denotes an amine functional substituent of the formula —R″Z, wherein R″ is a divalent alkylene radical of 3 to 6 carbon atoms or a radical of the formula —CH$_2$CH$_2$CH$_2$OCH$_2$CHOHCH$_2$— and Z is a monovalent radical selected from the group consisting of —NR$_2'''$, —NR'''(CH$_2$)$_2'''$; and

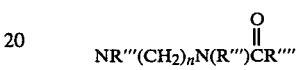

wherein R''' denotes hydrogen or an alkyl group of 1 to 4 carbons, R'''' denotes an alkyl group of 1 to 4 carbons and n is a positive integer from 2 to 6; z has a value of 0 or 1; x has an average value of 25 to 1000; y has an average value of 0 to 100 when z is 1, y has an average value of 1 to 100 when z is 0; when the proviso that in all cases y has an average value that is not greater than one tenth the average value of x; and (C) 3 to 30 percent by weight of a detersive surfactant selected from the group consisting of anionic surfactants and amphoteric surfactants, (D) 50 to 96.7 percent by weight of water.

The invention further relates to a method of preparing a shampoo composition comprising as a first step, mixing (A) and (B) and as a second step, mixing the blend of (A) and (B) with (C) and (D).

DETAILED DESCRIPTION OF THE INVENTION

The amine functional siloxane polymers used in the present invention are known materials which are generally insoluble in aqueous systems. The aqueous shampoo compositions of the present invention, however, are based on the discovery of a way to form clear, stable solutions of the siloxane polymers in water.

Specifically, it was discovered that blends of the siloxane polymer and nonionic surfactants of the alkanolamide or amine oxide type would readily dissolve in aqueous solutions containing the typical anionic and amphoteric detergents used in shampoos. The ready solubility of the siloxane/surfactant blend in water is surprising since the blend itself is not clear. The nonionic surfactant and siloxane polymer are incompatible and form only an opaque blend when they are mixed. Moreover, attempts to dissolve the siloxane polymer in aqueous solutions already containing the nonionic surfactant are unsuccessful. However, the opaque blend of siloxane and surfactant dissolves when added to aqueous systems to form clear solutions that are stable for extended periods of time.

Although the exact manner in which the siloxane polymer is dissolved within the aqueous system is not completely understood, it does appear that a solution instead of a microemulsion is formed. For example, the solutions do not have the characteristic bluish appearance of microemulsions in reflected light. In addition, the solutions are essentially clear and transparent in contrast to the somewhat translucent appearance which is more typical for microemulsions. It is believed that the blend of components in some way facilitates the spontaneous organizing of the siloxane into minute units stably dissolved in the aqueous system. This description of the dissolution process is offered only as a possible explanation and is not intended to further limit or define the present invention.

The water-based shampoos of the present invention are stable, homogeneous, and substantially transparent solutions containing an amine functional siloxane polymer as a hair conditioning component. Any predominately methylsiloxane polymer bearing an appropriate level of amine containing organic substituents is believed suitable for use in the shampoos of the present invention. The term, "predominately methylsiloxane" is intended to include any siloxane polymer wherein the majority of the nonfunctional organic substituents on silocon are methyl groups. It is preferred for maximum stability that the siloxane polymers be terminated by triorganosilyl groups, but it is anticipated that siloxane polymers with low levels of silanol or alkoxysilicon groups can function essentially equivalently in the shampoo compositions of this invention.

The level of amine containing organic substituents in the siloxane polymers may vary from one per polymer molecule up to about one for every ten siloxane units in the polymer molecule. Siloxanes with higher levels of amine containing substituents may be employed in shampoos, but generally are less preferred because of their higher cost and lack of any advantage relative to less substituted siloxanes.

The siloxanes which have been found most suitable for use in the shampoos of the present invention are represented by the general formula $$R_{3-z'}Q_zSiO[R_2'SiO]_x[R'QSiO]_ySiQ_zR_{3-z'}$$

wherein R' denotes an alkyl group of 1 to 4 carbons or a phenyl, with the proviso that at least 50 percent of the total R' groups are methyl; Q denotes an amine functional substituent; and z has the value of 0 or 1. Useful R' groups, for example, may be selected independently from among radicals such as methyl, ethyl, propyl, isopropyl, butyl, isobutyl, and phenyl as long as 50 percent of the R' groups are methyl.

Useful siloxane polymers may have amine functional substituents attached to terminal siloxane units or attached to siloxane units as pendent groups along the polymer chain. In the above siloxane formula, when z has the value of 0, y has an average value of 1 to 100 and the siloxane contains only pendent amine functional substituents. When z has the value 1, y has an average value of 0 to 100 and the siloxane may have only terminal amine functional substituents or both terminal and pendent amine functional substituents.

The most useful amine functional substituents for the siloxane polymers of the present invention can be represented by the general formula

—R"Z wherein R" is a divalent alkylene radical of 3 to 6 carbon atoms or a radical of the formula —CH₂CH₂C-H₂OCH₂CHOHCH₂— and Z is a monovalent amine radical selected from the group consisting of —NR₂''', —NR'''(CH₂)ₙNR₂''', and

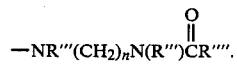

The alkylene radicals denoted by R" may include, for example, trimethylene, tetramethylene, pentamethylene, —CH₂CHCH₃CH₂—, and —CH₂CH₂CHCH₃CH₂—. Siloxane polymers wherein the R" radical denotes —CH₂CH₂CH₂OCH₂CHOHCH₂— are also useful in the present invention. However, siloxanes wherein R" is a trimethylene or an alkyl substituted trimethylene radical such as —CH₂CHCH₃CH₂— are preferred because of ease of synthesis and availability.

In the formula for the amine functional substituent, Z represents an amine radical that may be substituted or unsubstituted. The preferred amine radicals include —NR₂''', —NR'''(CH₂)ₙNR₂''' and

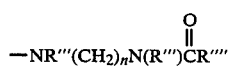

wherein n is a positive integer from 2 to 6, or more preferably n is 2 or 3, R''' denotes hydrogen or an alkyl group of 1 to 4 carbon atoms, and R'''' denotes an alkyl group of 1 to 4 carbon atoms. Alkyl groups of 1 to 4 carbon atoms as represented by R''' and R'''' include, for example, methyl, ethyl, propyl, butyl, isopropyl and isobutyl. For example, useful Z radicals include, among others, the unsubstituted amine radical —NH₂; alkyl substituted amine radicals such as —NHCH₃, —NHCH₂CH₂CH₂CH₃, and —N(CH₂CH₃)₂; aminoalkyl substituted amine radicals such as —NHCH₂CH₂NH₂, —NH(CH₂)₆NH₂, and —NHCH₂CH₂CH₂N(CH₃)₂; and amidoalkyl substituted amine radicals such as

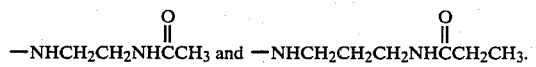

The siloxane polymers which are useful in the present invention may vary widely in viscosity and degree of polymerization. In the general siloxane formula $$R_{3-z'}Q_zSiO[R_2'SiO]_x[R'QSiO]_ySiQ_zR_{3-z'},$$

for example, x may vary from an average value of 25 to 100 and y may vary from 0 to 100 when z is 1 and from 1 to 100 when z is 0. However, siloxane polymers wherein the value of x+y is within the range of 50 to 500 are generally preferred in the shampoo compositions of the present invention because siloxane polymers within this range of polymerization generally provide the most desirable properties or conditioning on hair.

The amine functional siloxane polymer should be present in the shampoo compositions in an amount from about 0.1 to 10 weight percent or more preferably about 0.3 to 5 weight percent based on the total weight of the composition. At concentrations below the minimum concentration disclosed herein, the amount of the siloxane polymer that is deposited on the hair is insufficient to impart any significant conditioning to the hair. Concentrations greater than the maximum concentration disclosed are inefficient since there is little if any increase in siloxane deposited on the hair and consequently no further improvements in hair conditioning.

Methods for preparing the amine functional siloxane polymers that are employed in the shampoo compositions according to this invention are well known in the art. For example, known polydiorgansiloxane polymers bearing reactive groups such as ≡SiH, ≡SiCH₂CH₂CH₂Cl, or

may be reacted with CH₂=C(CH₃)CH₂NHCH₂CH₂NH₂, ethylenediamine or dimethylamine, respectively, to provide suitable siloxanes. Alternatively suitable aminoalkyl substituted polydiorganosiloxanes may be prepared from aminoalkyl substituted silanes or siloxanes using well known methods of hydrolysis and equilibration. It is usually preferred, for example, to prepare aminoalkyl substituted polydimethylsiloxanes by hydrolyzing a silane such as H₂NCH₂CH₂NHCH₂CHCH₃CH₂Si(CH₃)—(OCH₃)₂ in excess water and equilibrating the resulting hydrolyzate with dimethylcyclopolysiloxane and decamethyltetrasiloxane using a base catalyst such as KOH.

The shampoo compositions of this invention contain from 3 to 30, preferably 6 to 25, weight percent of a detersive surfactant selected from the group consisting of anionic and amphoteric surfactants. The detersive surfactant functions as a foaming and cleansing agent in the shampoo composition. The identity of the detersive surfactant in the shampoo compositions of this invention is not critical as long as the surfactant system in the shampoo is capable of cleaning the hair and providing an acceptable level of foam on the hair. The surfactant system may comprise one or more water soluble detergents, i.e., an anionic or amphoteric surfactant which produces an acceptable level of foam and cleaning for the hair.

Anionic detergents are preferred since they provide richer, denser foams than other types of detergents at comparable concentrations. It is desirable for that reason that the surfactant system contain at least one anionic detergent. Suitable anionic detergents include sulfonated and sulfated alkyl, aralkyl and alkaryl anionic detergents; alkyl succinates; alkyl sulfosuccinates and N-alkoyl sarcosinates. Especially preferred are the sodium, magnesium, ammonium, and the mono-, di- and triethanolamine salts of alkyl and aralkyl sulfates as well as these salts of alkaryl sulfonates. The alkyl groups of the detergents generally have a total of from about 12 to 21 carbon atoms, may be unsaturated, and are preferably fatty alkyl groups. The sulfates may be sulfate ethers containing one to ten ethylene oxide or propylene oxide units per molecule. Preferably, the sulfate ethers contain 2 to 3 ethylene oxide units.

Typical anionic detergents include, among ethers, sodium lauryl sulfate, sodium lauryl ether sulfate, ammonium lauryl sulfate, triethanolamine lauryl sulfate, sodium C14–16 olefin sulfonate, ammonium pareth-25 sulfate (ammonium salt of a sulfated polyethylene glycol ether of a mixture of synthetic C12–15 fatty alcohols), sodium myristyl ether sulfate, ammonium lauryl ether sulfate, disodium monooleamidosulfosuccinate, ammonium lauryl sulfosuccinate, sodium dodecylbenzene sulfonate, triethanolamine dodecylbenzene sulfonate and sodium N-lauroyl sarcosinate. The most preferred anionic detergents are the lauryl sulfates, particularly monoethanolamine, triethanolamine, ammonium and sodium lauryl sulfates. Sodium lauryl ether sulfate is also very suitable for use in the compositions of this invention.

Surfactants generally classified as amphoteric or ampholytic detergents include, among others, cocoamphocarboxyglycinate, cocoamphocarboxypropionate cocobetaine, N-cocamidopropyldimethylglycine, and N-lauryl-N'-carboxymethyl-N'-(2-hydroxyethyl)ethylenediamine. Other suitable amphoteric detergents include the quaternary cycloimidates, betaines, and sultaines disclosed in U.S. Pat. No. 3,964,500. The quaternary cycloimidates have the general structure:

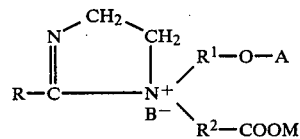

wherein R is an aliphatic hydrocarbon radical having about 9 to about 17 carbon atoms; R¹ and R² are each dependently (a) a divalent alkylene radical having 1 to 4 carbon atoms, (b) a hydroxy-substituted divalent alkylene radical having 2 to 4 carbon atoms, (c) a divalent alkylene radical having 2–4 carbon atoms wherein said alkylene radical contains an ether or a keto linkage, and (d) a hydroxy-substituted divalent alkylene radical having 2–4 carbon atoms wherein said alkylene radical contains an ether or a keto linkage; M is a water-solubilizing cation; A is (a) M, (b) —CH₂COOM (c) —C₂H₄OCH₂COOM or (d) —C₂H₄COOM; and B is (a) OH⁻, (b) C₁₂H₂₅OSO₃⁻, or (c) C₁₂H₂₅—C₆H₄—SO₃⁻.

Particularly preferred amphoteric surfactants are the substituted quaternary hydroxy cycloimidinic acid alkali metal alcoholates described in U.S. Pat. No. 2,528,378 and which have the generic structure:

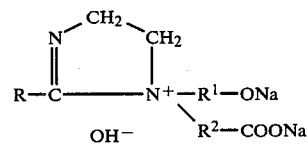

wherein R is an aliphatic hydrocarbon radical having about 9–17 carbon atoms, R¹ and R² represent divalent alkylene groups having 1 to 4 carbon atoms, and may be the same or different.

The most preferred of the amphoteric surfactants are the substituted quaternary hydroxy cycloimidinic acid alkali metal alkoxymethyl carboxylates described in U.S. Pat. No. 2,781,354, and which have the generic structure:

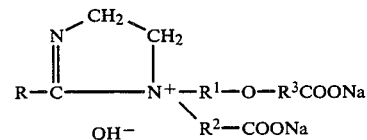

wherein R is an aliphatic hydrocarbon radical having about 9 to about 17 carbon atoms, R¹ and R² are as defined above, and R³ is a divalent alkylene group having 1 to 2 carbon atoms.

A useful compound is one having the foregoing structure wherein R has 11 carbon atoms, $R^1$ has 2 carbon atoms and $R^2$ and $R^3$ each have 1 carbon atom.

The betaines may have the structure:

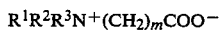

$$R^1R^2R^3N^+(CH_2)_mCOO^-$$

wherein $R^1$ is an alkyl group having about 12 to about 18 carbon atoms or a mixture thereof, $R^2$ and $R^3$ are independently lower alkyl groups having 1 to 3 carbon atoms, and m is an integer from 1 to 4. Specific betaines useful in the products of the invention are for example alpha-(tetradecyldimethylammonio)acetate, beta-(hexadecyldiethylammonio)propionate, and gamma-(dodecyldimethylammonio)butyrate.

The sultaines may have the structure:

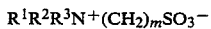

$$R^1R^2R^3N^+(CH_2)_mSO_3^-$$

wherein $R^1$, $R^2$, $R^3$, and m are defined as above. Specific useful sultaines are for example 3-(dodecyldimethylammonio)propane-1-sulfonate, and 3-(tetradecyldimethylammonio)ethane-1-sulfonate.

The shampoo compositions of this invention contain from 0.1 to 10 weight percent of a nonionic surfactant which solubilizes amine functional siloxane polymers in aqueous solutions of the detersive surfactants. The nonionic surfactants useful in the present invention are selected from the group consisting of fatty acid alkanolamide and amine oxide surfactants.

The fatty acid alkanolamides are nonionic surfactants obtained by reacting alkanolamines such as monoethanolamine, diethanolamine, monoisopropanolamine, or diisopropanolamine with a fatty acid or fatty acid ester to form the amide. The hydrophobic portion of the nonionic surfactant is provided by a fatty acid hydrocarbon chain which generally has from 10 to 21 carbon atoms. The fatty acid alkanolamide surfactants include, for example, fatty acid diethanolamides such as isostearic acid diethanolamide, lauric acid diethanolamide, capric acid diethanolamide, coconut fatty acid diethanolamide, linoleic acid diethanolamides, myristic acid diethanolamide, oleic acid diethanolamide, and stearic acid diethanolamide; fatty acid monoethanolamides such as coconut fatty acid monoethanolamide; and fatty acid monoisopropanolamides such as oleic acid monoisopropanolamide and lauric acid monoisopropanolamide.

The amine oxides are well known nonionic surfactants usually obtained by oxidizing a tertiary amine to form the amine oxide. They are sometimes also referred to as polar nonionic surfactants. Amine oxide surfactants include, for example, the N-alkyl amine oxides such as N-cocodimethylamine oxide, N-lauryl dimethylamine oxide, N-myristyl dimethylamine oxide, and N-stearyl dimethylamine oxide; the N-acyl amine oxides such as N-cocamidopropyl dimethylamine oxide and N-tallowamidopropyl dimethylamine oxide; and N-alkoxyalkyl amine oxides such as bis(2-hydroxyethyl) C12-15 alkoxypropylamine oxide. The hydrophobic portion of the amine oxide surfactants is generally provided by a fatty hydrocarbon chain containing from 10 to 21 carbon atoms.

Other examples of fatty acid alkanolamide and amine oxide surfactants, well known to the art, may be found in the literature such as "Surfacte Active Agents" by Schwartz and Perry and "Surface Active Agents and Detergents" by Schwartz, Perry and Berch, both Interscience Publishers, New York, N.Y., the disclosures of which are hereby incorporated by reference.

For the purposes of this invention the alkanolamide and amine oxide surfactants which most effectively solubilize amine functional siloxane polymers over a range of concentrations and conditions are preferred. In general, the fatty acid diethanolamides and N-alkyl dimethylamine oxides are preferred for use in the shampoo compositions because of their superior ability to solubilize the amine functional siloxane polymers. Especially preferred are the fatty acid diethanolamides and N-alkyl dimethylamine oxides where the fatty hydrocarbon chain contains from 10 to 18 carbon atoms. For example, especially preferred nonionic surfactants include lauric acid diethanolamide, N-lauryl dimethylamine oxide, coconut acid diethanolamide, myristic acid diethanolamide, and oleic acid diethanolamide.

The shampoo compositions of the present invention are aqueous solutions and generally contain from about 50 to 96.7 percent by weight water. It is preferred, however, that the shampoo compositions contain from about 60 to 90 percent by weight water.

The hair shampoo compositions of the present invention are prepared by first mixing the fluid siloxane polymer with the nonionic surfactant until a relatively homogeneous, but opaque blend is obtained. The mixing may be carried out at room temperature or at elevated temperatures. When the nonionic surfactant is solid or wax-like at room temperature, it is usually preferred to heat the surfactant until it is liquified to facilitate mixing with the siloxane polymer fluid.

The siloxane/surfactant blend is then mixed into the aqueous system. The blend may be mixed into water and then combined with an aqueous solution of detersive surfactants or the blend may be mixed directly into the aqueous solution of detersive surfactants.

Other adjuvants may be added to the shampoo compositions of this invention such as thickeners, perfumes, colorants, electrolytes, pH control ingredients, antimicrobials, antioxidants, ultraviolet light absorbers and medicaments. For example, it is usually preferred to employ a thickener in the shampoo compositions to facilitate the hand application of the shampoo to the hair. Thickeners are preferably used in sufficient quantities to provide a convenient viscosity. For example, viscosities within the range of 400 to 6000 cps or more preferably in the range of 1000 to 4000 cps as measured at 25° C. are usually suitable.

Suitable thickeners include, among others, sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose and starch amylose, locust bean gum, electrolytes such as NaCl, saccharides such as fructose and glucose, and derivatives of saccharides such as PEG-120 methyl glucose dioleate. Preferred thickeners include the cellulose derivatives and saccharide derivatives. The glucose derivative, PEG-120 methyl glucose dioleate, is especially preferred in the shampoos of the present invention.

The perfumes which can be used in the shampoo compositions are the cosmetically acceptable perfumes and they may be present in amounts which vary from 0.1 to 0.5 percent by weight.

Colorants are used to confer a color to the shampoo and may generally be used in an amount from 0.001 to 0.5 percent by weight.

Although not required, it is preferred to employ an acid to adjust the pH within the range of 5 to 9 or more preferably within the range of 6 to 8 in the shampoo compositions of this invention. Any water soluble acid such as a carboxylic acid or a mineral acid is suitable. For example, suitable acids include mineral acids such as hydrochloric, sulfuric, and phosphoric; monocarboxylic acid such as acetic acid, lactic acid, or propionic acid; and polycarboxylic acids such as succinic acid, adipic acid and citric acid.

The shampoos of the present invention are aqueous solutions. The term "solution" as employed in this specification means that the essential components are homogeneously mixed and that the components are subdivided to such an extent that there is no appearance of light scattering visible to the naked eye when a one inch diameter bottle of the mixture is viewed in sunlight. As well known in the art, light scattering which is often referred to as the Tyndall Effect is related to the particle size of components dispersed within a medium. Typical macroemulsions appear opaque white while microemulsions with smaller particles appear bluish and translucent because of light scattering.

While the formation of the solution of essential components is believed critical to obtain a uniform and proper level of deposition of the siloxane conditioning component on the hair, it is recognized that other optional adjuvants may not need to be dissolved to fulfill their intended function in the shampoo. As long as such other nondissolved components do not destabilize the aqueous solution of essential components, such nonclear shampoo compositions are essentially equivalent in function to the shampoo compositions of this invention. For example, a shampoo composition of this invention which is made opaque by the addition of a pearling agent such as glycol distearate is expected to function equivalently to the clear shampoo compositions without the pearling agent.

The shampoo compositions of the present invention may be in the form of a gel, paste, or a freely pourable liquid. The shampoo compositions can be used on the hair of humans or animals to cleanse and improve the appearance of their hair or coats, respectively. The shampoos are expected to be used by the usual method of adding the shampoo to the hair, massaging the shampoo into the hair and removing the shampoo from the hair by rinsing with water.

The shampoos of the present invention have superior stabilities during storage and shipping. During the shampooing operation, the shampoos provide a rich and billowy lather. After the shampoo is rinsed from the hair, the hair is left with a clean feeling but at the same time it is conditioned so that it is more easily combed than hair washed in shampoos without the siloxane conditioning component.

An advantage of the shampoo compositions of this invention is that the washed hair retains less water when the shampoo is rinsed out. Since the hair contains less water, it is then easier and faster to dry.

Another advantage of the shampoo compositions of the present invention is that the siloxane conditioning component is quite effectively delivered, i.e., deposited on the hair from the shampoo composition. In view of the fact that quaternary nitrogen containing conditioning components of the prior art do not generally deposit well from shampoos containing anionic detersive surfactants, it is surprising that the amine functional siloxane polymer is so effectively deposited from shampoos containing the anionic detersive surfactants. Since anionic detergents are preferred for reasons already discussed, the shampoo compositions of the present invention containing anionic detergents provide a unique and advantageous combination of superior foaming and conditioning in one product.

In view of the superior conditioning provided by the amine functional siloxane polymer in the shampoo compositions of the present invention, it is frequently neither necessary nor desirable that additional hair conditioners be used in the shampoo.

Consequently, it is preferred that the shampoo compositions of this invention consist essentially of the detersive surfactant, the nonionic surfactant selected from the group consisting of alkanolamide and amine oxide surfactants, the amine functional siloxane polymer, water, and a thickener. If for special purposes additional conditioners are desired, they may be added. For example, any of the well-known organic cationic hair conditioning components that are water soluble may be added. Some cationic conditioning components that may be used in the shampoos of the present invention to provide additional hair grooming include quaternary nitrogen derivatives of cellulose ethers, homopolymers of dimethyldiallylammonium chloride, copolymers of acrylamide and dimethyldiallylammonium chloride, homopolymers or copolymers derived from acrylic acid or methacrylic acid containing cationic nitrogen functional groups attached to the polymer via ester or amide linkages, polycondensation products of N,N'-bis-(2,3-epoxypropyl)-piperazine or of piperazine-bis-acrylamide and piperazine, poly-(dimethylbutenylammonium chloride)-$\alpha,\omega$-(triethanolammonium) chloride, and copolymers of vinylpyrrolidone and acrylic acid esters with quaternary nitrogen functionality. The above cationic organic polymers and others are described in more detail in U.S. Pat. No. 4,240,450 which is hereby incorporated by reference to further describe the cationic organic polymers.

The method of this invention is further illustrated by the following examples which teach the best mode for carrying out the invention; however, the examples should not be regarded as limiting the invention which is delineated by the appended claims. All parts and percentages are by weight unless otherwise stated.

Amine neutral equivalent (A.N.E.) denotes the parts by weight of a material that is required to provide 14.007 parts by weight of amine and/or amine salt nitrogen. It was determined by dissolving the sample in a mixture of toluene and glacial acetic acid and titrating the solution anhydrously with perchloric acid to a methyl violet endpoint.

EXAMPLE 1

A mixture of 57 g (0.26 mols) of $CH_3(CH_3O)_2SiCH_2CHCH_3CH_2NHCH_2CH_2NH_2$, 902.9 g (12.17 mols) of dimethylsiloxane units, 40.2 g (0.13 mols) of $(CH_3)_3SiOSi(CH_3)_2OSi(CH_3)_2OSi(CH_3)_3$, 4.7 g (0.26 mols) of water, and 6.3 g ($2.59 \times 10^{-3}$ mols $K^+$, 0.08 mols dimethylsiloxane units) of potassium silanolate was heated to 150° C. over a two hour period and maintained at that temperature for an additional 2.5 hours, to remove the methanol and water and to equilibrate the siloxane units. The product was cooled, treated with 0.16 g ($2.7 \times 10^{-3}$ mols) of acetic acid to neutralize the potassium catalyst, and filtered. The fluid product had a viscosity of 124 cs at 25° C. and an A.N.E. of 1930. The product is a mixture of approximately 10 percent cyclic polysiloxanes and 90 percent linear polysiloxanes. The linear siloxane polymer generally conforms to the average formula

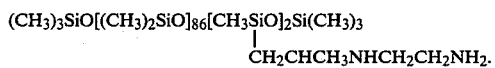

$(CH_3)_3SiO[(CH_3)_2SiO]_{86}[CH_3SiO]_2Si(CH_3)_3$
$\quad\quad\quad\quad\quad\quad\quad\quad\quad\quad\quad\quad |$
$\quad\quad\quad\quad\quad\quad\quad\quad\quad\quad\quad\quad CH_2CHCH_3NHCH_2CH_2NH_2.$

EXAMPLE 2

A mixture of 122.6 g (0.556 mols) of $CH_3(CH_3O)_2$-$SiCH_2CHCH_3CH_2NHCH_2CH_2NH$, 1964.2 g (26.47 mols) of dimethylsiloxane units, 86.85 g (0.279 mols) of $(CH_3)_3SiOSi(CH_3)_2OSi(CH_3)_2OSi(CH_3)_3$, 9.0 g (0.5 mols) of $H_2O$, and 3.6 g of 40% aqueous potassium hydroxide was heated to 150° C. for 4 hours to hydrolyze the silicon-methoxy bonds, to remove methanol and water, and to equilibrate the siloxane units. The product was cooled to 30° C. and 62.33 g (0.612 mols) of acetic anhydride was added. The mixture was heated to 150° C. for 2 hours and then stripped to 150° C./10 mm Hg. The product was cooled and filtered to yield a light yellow fluid having a viscosity at 25° C. of 311 cs and an A.N.E. of 4896. The nonvolatile linear siloxane polymer obtained conforms generally to the average formula

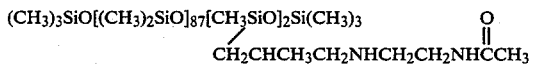

but the product also contains some polymer that is acylated at the secondary nitrogen as well as the primary nitrogen.

EXAMPLE 3

A mixture of 3678.2 g (2.048 mols amine equivalent) of siloxane polymer prepared by the procedure of Example 1 and 104.5 g (1.024 mols) acetic anhydride were mixed for 20 hours at room temperature. The mixture was filtered to yield a clear yellow fluid with viscosity of 897 cs at 25° C. and an A.N.E. of 3666. The product is a mixture of approximately 10 percent cyclic polysiloxanes and 90 percent linear polysiloxanes. The linear polysiloxane polymer generally conforms to the average formula

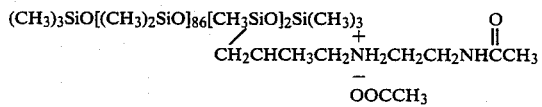

EXAMPLE 4

Shampoo compositions containing two different amine functional silicone polymers were prepared by the following procedure. Silicone polymer (2 parts) and lauramide DEA (lauric acid amide of diethanolamine, 6 parts) were combined, heated until liquified, and manually stirred until a homogeneous, milk-white, opaque blend was obtained. The silicone/lauramide DEA blend was added with stirring to a surfactant solution of ammonium lauryl sulfate (9 parts) in water (about 60 parts). A clear solution resulted which was thickened by the addition of 2.5 parts of PEG-120 methyl glucose dioleate (a methyl glucoside derivative with two polyoxyethylene substituent groups containing a total of 120 oxyethylene units). The thickener was heated to about 60° C. to facilitate its mixing into the shampoo composition. The pH of the composition was adjusted to 6.8 with 25% aqueous citric acid solution and sufficient additional water was added to make 100 parts of shampoo composition.

Shampoo Composition I contained the siloxane polymer prepared in Example 1 and Shampoo Composition II contained the siloxane polymer prepared in Example 2.

The conditioning efficacy of each shampoo composition was evaluated by measuring the force required to comb wet hair both before and after shampooing with the compositions. An equivalent shampoo composition without silicone polymer was also tested for comparison.

Combing forces were measured on an Instron testing apparatus adapted with a hard rubber comb. Both peak combing force and average combing load (ACL) were determined for each hair tress. The average combing load was determined by integrating the total combing force and dividing by the length of hair combed in centimeters and is reported as a relative numerical value. The average combing load is a measurement of the average force required to comb hair and is believed more indicative of the overall combing and tangling characteristics of hair than the peak combing force.

Tresses (12 g) of virgin European brown hair were prepared for testing by soaking for 12 to 30 minutes in distilled water and then combing by hand until tangle-free. Each tress was then dipped three times into a distilled water bath to produce a relatively uniform level of tangling. Each tress was then combed on the Instron apparatus to determine the untreated combing force.

Hair tresses were shampooed using 0.4 g of the test shampoo. The shampoo was lathered on the hair with rubbing for 60 seconds and then rinsed off in running 40° C. tap water for 60 seconds. Each tress was again detangled by hand combing, retangled by dipping three times in a water bath, and combed on the Instron apparatus. After the shampoo treatment, the dentangling, retangling, and combing force measurement sequence was repeated four times on each tress. The ACL for each treated tress is an average of these four separate measurements. The difference between the average combing load (ACL) before and after the shampoo treatment of the hair is shown in Table 1. The shampoo treatment in each case increased the average force required to comb the hair, but Shampoo Compositions I and II containing the silicone polymer generally produced less of an increase than the control.

TABLE 1
COMBING CHARACTERISTICS BEFORE AND AFTER SHAMPOO TREATMENT

| Shampoo | Tress No. | Average Combing Load | | |
|---|---|---|---|---|
| | | Before | After | Difference |
| Control | 1 | 333 | 768 | 435 |
| Control | 2 | 363 | 820 | 457 |
| Control | 3 | 348 | 714 | 366 |
| I | 4 | 435 | 516 | 81 |
| I | 5 | 283 | 590 | 307 |
| I | 6 | 303 | 457 | 154 |
| II | 7 | 356 | 749 | 393 |
| II | 8 | 467 | 655 | 188 |
| II | 9 | 281 | 493 | 212 |

EXAMPLE 5

The conditioning efficacy of Shampoo Compositions I and II from Example 4 were further evaluated on a second lot of virgin European brown hair. This second lot of hair tended to be less tangly after shampooing than the lot used in Example 4. The evaluation was carried out by the same procedure described in Example 4. The differences between the relative ACL values before and after the shampoo treatments are shown in Table 2. Again the shampoo compositions containing the silicone polymers generally produced less of an increase than the control shampoo. Moreover, two tresses showed an actual decrease in relative ACL when shampooed with compositions of this invention.

Silicone deposition on the hair was demonstrated by determining the amount of silicon on the hair using atomic absorption analysis of solvent extractions of enzyme digested portions of treated hair tresses. Results are reported in parts per million silicon per gram of hair. The silicon detected on untreated hair is believed to result from the use of silicone RTV to bind the root ends of the hair tresses during the combing tests. However, the data demonstrates a significant increase in silicon on the hair after treatment with shampoos containing the silicone polymers.

TABLE 2

COMBING CHARACTERISTICS BEFORE AND AFTER SHAMPOO TREATMENT

| Shampoo | Tress No. | Before | After | Difference | PPM Si/ gm Hair |
|---|---|---|---|---|---|
| Control | 1 | 193 | 428 | 235 | |
| Control | 2 | 245 | 334 | 89 | 46 ± 5 |
| Control | 3 | 127 | 316 | 189 | |
| I | 4 | 252 | 305 | 53 | 65 ± 5 |
| II | 5 | 189 | 318 | 129 | |
| II | 6 | 350 | 326 | −24 | |
| II | 7 | 260 | 305 | 45 | 71 ± 5 |
| II | 8 | 294 | 330 | 36 | |
| II | 9 | 348 | 336 | −12 | |
| II | 10 | 307 | 379 | 72 | |

EXAMPLE 6

After about four months of shelf aging, the shampoo compositions of Example 4 were again evaluated on relatively tangly hair from the same lot of virgin European brown hair as used in Example 4. The testing procedure described in Example 4 was followed and the differences between the relative ACL values before and after the shampoo treatments are shown in Table 3. Except for the results with tresses 8 and 9, which seem to be out of line with the rest of the data because of low initial ACL values, the silicone containing shampoos produced less combing force increase than the control shampoo.

TABLE 3

COMBING CHARACTERISTICS BEFORE AND AFTER TREATMENT WITH AGED SHAMPOO COMPOSITIONS

| Shampoo | Tress No. | Before | After | Difference |
|---|---|---|---|---|
| Control | 1 | 735 | 837 | 102 |
| Control | 2 | 768 | 836 | 68 |
| Control | 3 | 790 | 854 | 64 |
| I | 4 | 925 | 766 | −159 |
| I | 5 | 756 | 809 | 53 |
| I | 6 | 823 | 830 | 7 |
| II | 7 | 850 | 819 | −31 |
| II | 8 | 585* | 822 | 237 |
| II | 9 | 479* | 755 | 276 |

*Low values may indicate an error or irregularity associated with the initial measurement of ACL for these tresses.

EXAMPLE 7

Using the method of Example 4, three shampoo compositions of the present invention and three comparison shampoo compositions were prepared identically except for the differing conditioning components employed. As in Example 4 each shampoo was based on a formulation of 9 parts ammonium lauryl sulfate, 6 parts lauramide DEA, 2.5 parts PEG-120 methyl glucose dioleate and, if present, 2 parts of conditioning component.

Shampoo Composition III contained as the conditioning component the partially acylated amine functional siloxane polymer prepared in Example 2. Shampoo Composition IV contained the acylated but unstripped siloxane polymer prepared in Example 3. Shampoo Composition V contained a siloxane polymer prepared by the procedure of Example 1 with the linear siloxane polymer portion generally conforming to the average formula

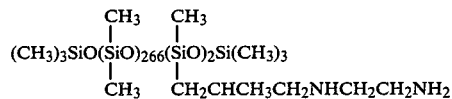

Comparison Shampoo A contained polyquaterium-10, a polymer of hydroxyethyl cellulose reacted with epichlorohydrin and quaternized with trimethylamine. Polyquaternium-10 is a well known, water soluble organic hair conditioning component. Quaternary ammonium derivatives of cellulose ether are further described in U.S. Pat. No. 4,240,450, the disclosure of which is hereby incorporated by reference.

Comparison Shampoo B contained an aqueous cationic emulsion copolymer of 99 mole percent dimethylsiloxane units and 1 mole percent N-(2-aminoethyl)-3-aminopropylsiloxane units. The copolymer contains hydroxyl groups attached to silicon atoms at chain terminating sites. An appropriate amount of the emulsion was added to the shampoo to provide 2 parts of the silicone polymer solids per 100 parts of shampoo composition. However, the silicone emulsion was not stable in the shampoo formulation and chunks or globules of apparently gelled silicone polymer separated from the mixture. These globules tended to stick to the sides of the container and could not be redispersed by normal stirring.

Comparison Shampoo C contained no siloxane conditioning component and was included in the testing as a control to determine the effect of a nonconditioning shampoo.

The conditioning efficacy of each shampoo composition was evaluated by measuring the force required to comb wet hair both before and after shampooing with the compositions. Combing forces were measured by the same procedure described in Example 4, except that the ACL was computer-determined directly in grams instead of in relative numerical values. No special effort was made during the testing of Comparison Shampoo B to assure a homogeneous sample, but the portions of this shampoo applied to hair tresses did contain both liquid and globular gel phases. The difference between the average combing load (ACL) before and after the shampoo treatments of the hair is shown in Table 4. In all cases, the shampoo compositions of this invention caused less of an increase in combing force than the control shampoo. The results with Comparison Shampoo B are not uniform with some apparent conditioning effect on one tress but little or no effect on another. Such inconsistency may well result from the nonhomogeneous nature of the composition.

TABLE 4
COMBING CHARACTERISTICS BEFORE AND AFTER SHAMPOO TREATMENT

| Shampoo | Tress No. | Average Combing Load (g) | | |
|---|---|---|---|---|
| | | Before | After | Difference |
| A | 1 | 194 | 255 | 61 |
| | 2 | 232 | 292 | 60 |
| | 3 | 286 | 262 | −24 |
| B | 4 | 287 | 409 | 122 |
| | 5 | 601 | 581 | −20 |
| | 6 | 268 | 520 | 252 |
| C | 7 | 270 | 538 | 268 |
| | 8 | 269 | 545 | 276 |
| | 9 | 143 | 571 | 428 |
| III | 10 | 403 | 453 | 50 |
| | 11 | 192 | 318 | 126 |
| | 12 | 271 | 429 | 158 |
| IV | 13 | 419 | 465 | 46 |
| | 14 | 312 | 479 | 157 |
| | 15 | 282 | 356 | 74 |
| V | 16 | 264 | 263 | −1 |
| | 17 | 215 | 312 | 97 |
| | 18 | 319 | 254 | −65 |

EXAMPLE 8

A shampoo composition was prepared using the amine functional silicone polymer prepared in Example 1. The silicone (2 parts) was dispersed in lauramide DEA (6 parts) by warming and mixing until a homogeneous but opaque blend was formed. The silicone/lauramide DEA blend was added with stirring to a surfactant solution of sodium lauryl ether sulfate (9 parts) in about 60 parts water. Sodium lauryl ether sulfate is the sodium salt of sulfated ethoxylated lauryl alcohol where the lauryl alcohol has been ethoxylated with an average of 1 to 4 moles of ethylene oxide. The pH of the composition was adjusted to 6.8 with 25% aqueous citric acid solution and sufficient additional water was added to make 100 parts of shampoo composition. The shampoo composition was clear and stable at room temperature. In an accelerated aging test, the shampoo composition remained stable and clear for six weeks at 50° C.

EXAMPLE 9

Another shampoo composition was prepared in the same manner as described in Example 8 except that 10 parts of alpha-olefin sulfonate was substituted for the sodium lauryl ether sulfate. The alpha-olefin sulfonate is a mixture of long chain sulfonate salts prepared by sulfonation of C 14-16 alpha-olefins and consists chiefly of sodium alkene sulfonates and sodium hydroxyalkane sulfonates. The shampoo composition was clear and stable at room temperature.

EXAMPLE 10

A shampoo composition containing amine functional silicone polymer from Example 1 was prepared as described in Example 4 except that 2 parts of N-cocamidepropyl dimethylamine oxide was used instead of the PEG-120 methyl glucose dioleate to thicken the composition. A second shampoo composition was prepared in the same manner but using 2 parts of dimethyl lauramine oxide as the thickener. Both shampoo compositions were stable at room temperature for at least three weeks.

EXAMPLE 11

Three shampoo compositions containing amine functional silicone polymer from Example 1 were prepared as described in Example 4 except that an equal weight of an alternate surfactant was substituted in each composition for one-half of the ammonium lauryl sulfate. The other surfactants used were N-cocamidopropyl dimethyl glycine, cocoamphocarboxyglycinate and sodium N-lauroyl sarcosinate. All three shampoo compositions remained clear and stable for at least three weeks at room temperature.

EXAMPLE 12

A series of shampoos were prepared as described in Example 4 containing dimethylsiloxane polymers varying in degree of polymerization (DP) and mole percent of amine functional siloxane units. The dimethylsiloxane polymers were prepared by the procedure of Example 1 with appropriate modification of the ratios of dimethylsiloxane units, trimethylsiloxane units and amine functional siloxane units. The nominal degree of polymerization is reported as the total number of siloxane units per two trimethylsiloxane end groups and is not adjusted for cyclic siloxane formation.

The conditioning efficacy of each shampoo was evaluated by measuring the force required to comb wet and dry hair both before and after shampooing with the compositions. For comprison, a control shampoo that was equivalent except for the absence of a siloxane conditioning component was also tested. Combing forces were measured by the same procedure described in Example 4, except that the ACL was computer-determined directly in grams instead of relative numerical values. The difference between combing load before and after shampooing the hair is shown in Table 5. In all cases, the shampoo compositions of this invention caused less of an increase in combing force for wet hair than the control shampoo.

TABLE 5
COMBING CHARACTERISTICS BEFORE AND AFTER SHAMPOOING

| Siloxane Polymer | | Hair Tress No. | Average Combing Load (g) | | | | | |
|---|---|---|---|---|---|---|---|---|
| Nominal DP | Mole Percent Amine Units | | Wet Hair | | | Dry Hair | | |
| | | | Before | After | Difference | Before | After | Difference |
| 100 | 2 | 1 | 233 | 704 | 471 | 74 | 100 | 26 |
| | | 2 | 243 | 680 | 437 | 85 | 95 | 10 |

TABLE 5-continued
COMBING CHARACTERISTICS BEFORE AND AFTER SHAMPOOING

| Siloxane Polymer Nominal DP | Mole Percent Amine Units | Hair Tress No. | Wet Hair Before | Wet Hair After | Wet Hair Difference | Dry Hair Before | Dry Hair After | Dry Hair Difference |
|---|---|---|---|---|---|---|---|---|
|  |  | 3 | 329 | 583 | 254 | 55 | 123 | 68 |
| 100 | 5 | 4 | 244 | 546 | 302 | 74 | 73 | −1 |
|  |  | 5 | 214 | 662 | 448 | 51 | 104 | 53 |
|  |  | 6 | 270 | 546 | 276 | 54 | 135 | 81 |
| 200 | 2 | 7 | 286 | 798 | 512 | 106 | 77 | −29 |
|  |  | 8 | 344 | 631 | 287 | 62 | 70 | 8 |
|  |  | 9 | 224 | 549 | 325 | 105 | 109 | 4 |
| 200 | 5 | 10 | 243 | 302 | 59 | 81 | 86 | 5 |
|  |  | 11 | 617 | 473 | −144 | 75 | 62 | −13 |
|  |  | 12 | 265 | 432 | 167 | 86 | 86 | 0 |
| Control | — | 13 | 348 | 953 | 605 | 64 | 96 | 32 |
|  |  | 14 | 255 | 867 | 612 | 81 | 91 | 10 |
|  |  | 15 | 220 | 864 | 644 | 59 | 101 | 42 |

EXAMPLE 13

A shampoo composition containing a nonionic amine oxide surfactant was prepared by the following procedure. Siloxane polymer from Example 1 (2 parts) and dimethyl lauramine oxide (6 parts) were mixed and warmed until a homogeneous, opaque blend was obtained. The siloxane/amine oxide blend was added with stirring to a surfactant solution of ammonium lauryl sulfate (10.9 parts) in water (25.5 parts). An aqueous solution of 2 percent hydroxypropylmethylcellulose (37 parts) and additional water (16.6 parts) were added and the pH adjusted to 6.8 with 25 percent aqueous citric acid. The shampoo was further thickened by the addition of PEG-120 methyl glucose dioleate (2 parts). The shampoo composition obtained was a clear solution.

That which is claimed is:

1. A conditioning shampoo composition comprising, in the form of a solution,
   (A) 0.1 to 10 percent by weight of a nonionic surfactant selected from the group consisting of fatty acid alkanolamide surfactants and amine oxide surfactants,
   (B) 0.1 to 10 percent by weight of an amine functional siloxane polymer represented by the general formula $$R_{3-z'}Q_zSiO[R_2'SiO]_x[R'QSiO]_ySiQ_zR_{3-z'}$$

wherein R' denotes an alkyl group of 1 to 4 carbons or a phenyl group, with the proviso that at least 50 percent of the total R' groups are methyl; Q denotes an amine functional substituent of the formula —R"Z, wherein R" denotes a divalent alkylene radical of 3 to 6 carbon atoms or a radical of the formula —$CH_2CH_2CH_2OCH_2CHOHCH_2$— and Z denotes a monovalent radical selected from the group consisting of —$NR_2'''$, —$NR'''(CH_2)_nNR_2'''$, and

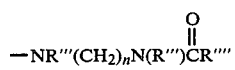

wherein R''' denotes hydrogen or an alkyl group of 1 to 4 carbons, R'''' denotes an alkyl group of 1 to 4 carbons, and n is a positive integer from 2 to 6; z has a value of 0 or 1; x has an average value of 25 to 1000; y has an average value of 0 to 100 when z is 1, y has an average value of 1 to 100 when z is 0; with the proviso that in all cases y has an average value that is not greater than one tenth the average value of x; and
   (C) 3 to 30 percent by weight of a detersive surfactant selected from the group consisting of anionic surfactants and amphoteric surfactants,
   (D) 50 to 96.7 percent by weight of water.

2. The composition in accordance with claim 1 wherein the detersive surfactant is an anionic surfactant selected from the group consisting of fatty alkyl sulfates and fatty alkyl sulfate ethers containing one to ten ethylene oxide or propylene oxide units.

3. The composition in accordance with claim 1 wherein the detersive surfactant is an alpha-olefin sulfonate.

4. The composition in accordance with claim 2 wherein the nonionic surfactant is a fatty acid alkanolamide in which the hydrocarbon chain of the fatty acid has from 10 to 21 carbons.

5. The composition in accordance with claim 4 wherein the fatty acid alkanolamides are selected from the group consisting of diethanolamides, monoethanolamides and monoisopropanolamides.

6. The composition in accordance with claim 5 wherein the fatty acid alkanolamide is a diethanolamide.

7. The composition in accordance with claim 6 wherein the hydrocarbon chain of the fatty acid alkanolamide has from 10 to 18 carbon atoms.

8. The composition in accordance with claim 7 comprising 0.3 to 5 percent by weight of amine functional siloxane polymer.

9. The composition in accordance with claim 8 wherein the R' denotes methyl and R" denotes a divalent alkylene radical of 3 to 6 carbon atoms.

10. The composition in accordance with claim 9 wherein R" denotes a trimethylene radical or the —$CH_2CHCH_3CH_2$— radical.

11. The composition in accordance with claim 10 wherein Z denotes —$NR'''(CH_2)_nNR_2'''$ or

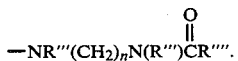

12. The composition in accordance with claim 11 wherein R''' denotes hydrogen, R'''' denotes methyl, and n is 2.

13. The composition in accordance with claim 12 wherein z is 0, and x+y has a value within the range of 50 to 500.

14. The composition in accordance with claim 13 wherein R" denotes —CH$_2$CHCH$_3$CH$_2$— and Z denotes —NHCH$_2$CH$_2$NH$_2$.

15. The composition in accordance with claim 13 wherein R" denotes —CH$_2$CHCH$_3$CH$_2$— and Z denotes

—NHCH$_2$CH$_2$NHCCH$_3$.

16. A method of preparing a shampoo composition comprising as a first step, mixing
   (A) 0.1 to 10 percent by weight of a nonionic surfactant selected from the group consisting of fatty acid alkanolamide surfactants and amine oxide surfactants and
   (B) 0.1 to 10 percent by weight of an amine functional siloxane polymer represented by the general formula

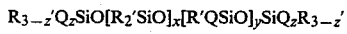
$R_{3-z'}Q_zSiO[R_2'SiO]_x[R'QSiO]_ySiQ_zR_{3-z'}$ wherein R' denotes an alkyl group of 1 to 4 carbons or a phenyl group, with the proviso that at least 50 percent of the total R' groups are methyl; Q denotes an amine functional substituent of the formula —R"Z, wherein R" denotes a divalent alkylene radical of 3 to 6 carbon atoms or a radical of the formula —CH$_2$CH$_2$CH$_2$OCH$_2$CHOHCH$_2$— and Z denotes a monovalent radical selected from the group consisting of —NR$_2$''', —NR'''(CH$_2$)$_n$NR$_2$''', and

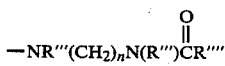
—NR'''(CH$_2$)$_n$N(R''')CR'''' wherein R''' denotes hydrogen or an alkyl group of 1 to 4 carbons, R'''' denotes an alkyl group of 1 to 4 carbons, and n is a positive integer from 2 to 6; z has a value of 0 or 1; x has an average value of 25 to 1000; y has an average value of 0 to 100 when z is 1, y has an average value of 1 to 100 when z is 0; with the proviso that in all cases y has an average value that is not greater than one tenth the average value of x; and as a second step, mixing the blend of (A) and (B) with (C) 3 to 30 percent by weight of a detersive surfactant selected from the group consisting of anionic surfactants and amphoteric surfactants and
(D) 50 to 96.7 percent by weight of water.

17. The method in accordance with claim 16 wherein the detersive surfactant is an anionic surfactant selected from the group consisting of fatty alkyl sulfates and fatty alkyl sulfate ethers containing one to ten ethylne oxide or propylene oxide units.

18. The method in accordance with claim 16 wherein the detersive surfactant is an alpha-olefin sulfonate.

19. The method in accordance with claim 17 wherein the nonionic surfactant is a fatty acid alkanolamide in which the hydrocarbon chain of the fatty acid has from 10 to 21 carbons.

20. The method in accordance with claim 19 wherein the fatty acid alkanolamides are selected from the group consisting of diethanolamides, monoethanolamides and monoisopropanolamides.

21. The method in accordance with claim 20 wherein the fatty acid alkanolamide is a diethanolamide.

22. The method in accordance with claim 21 wherein the hydrocarbon chain of the fatty acid alkanolamide has from 10 to 18 carbon atoms.

23. The method in accordance with claim 22 wherein 0.3 to 5 percent by weight of amine functional siloxane polymer is mixed with (A).

24. The method in accordance with claim 23 wherein the R' denotes methyl and R" denotes a divalent alkylene radical of 3 to 6 carbon atoms.

25. The method in accordance with claim 24 wherein R" denotes a trimethylene radical or the —CH$_2$CHCH$_3$CH$_2$— radical.

26. The method in accordance with claim 24 wherein Z denotes —NR'''(CH$_2$)$_n$NR$_2$''' or

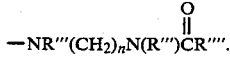
—NR'''(CH$_2$)$_n$N(R''')CR''''.

27. The method in accordance with claim 26 wherein R''' denotes hydrogen, R'''' denotes methyl, and n is 2.

28. The method in accordance with claim 27 wherein z is 0, and x+y has a value within the range of 50 to 500.

29. The method in accordance with claim 28 wherein R" denotes —CH$_2$CHCH$_3$CH$_2$— and Z denotes —NHCH$_2$CH$_2$NH$_2$.

30. The method in accordance with claim 28 wherein R" denotes —CH$_2$CHCH$_3$CH$_2$— and Z denotes

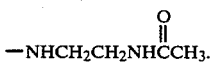
—NHCH$_2$CH$_2$NHCCH$_3$.

* * * * *

UNITED STATES PATENT AND TRADEMARK OFFICE
CERTIFICATE OF CORRECTION

PATENT NO. : 4,559,227

DATED : December 17, 1985

INVENTOR(S) : Grish Chandra, Gretchen S. Kohl, & James A. Tassoff

It is certified that error appears in the above-identified patent and that said Letters Patent is hereby corrected as shown below:

In Col. 2, line 8, "air" should read --hair--.

In Col. 3, line 14, "peallized" should read --pearlized--.

In Col. 4, line 16, "$-NR'''(CH_2)_2'''$" should read -- $-NR'''(CH_2)_n NR_2'''$ --.

In Col. 4, line 28, "when" should read --with--. (2nd occ.).

In Col. 5, line 20, "silocon" should read --silicon--.

In Col. 6, line 50, "100 and" should read --1000 and--.

In Col. 9, line 66, " "Surfacte " should read --"Surface--.

In Col. 12, line 36, "chloride)-α,ω-(triethanolammonium)" should read --chloride)-α,ω-bis-(triethanolammonium)--

In Col. 14, line 43, "dentangling" should read --detangling--.

In Col. 16, line 37, "polyquaterium-" should read -- polyquaternium- --.

In Col. 18, line 48, "comprison" should read --comparison--.

UNITED STATES PATENT AND TRADEMARK OFFICE
CERTIFICATE OF CORRECTION

PATENT NO. : 4,559,227
DATED : December 17, 1985
INVENTOR(S) : Grish Chandra, Gretchen S. Kohl, & James A. Tassoff It is certified that error appears in the above-identified patent and that said Letters Patent is hereby corrected as shown below:

In col. 22, line 9, "ethylne" should read --ethylene--.

Signed and Sealed this

Eighteenth Day of November, 1986

*Attest:*

DONALD J. QUIGG

*Attesting Officer*     *Commissioner of Patents and Trademarks*